United States Patent [19]

Richards et al.

[11] 4,045,441

[45] Aug. 30, 1977

[54] 7-(ALPHA-METHYL-ALPHA-ALKENYL)-SUBSTITUTED 8-HYDROXYQUINOLINES AND PROCESS FOR THE PREPARATION THEREOF

[75] Inventors: Harvey J. Richards, Columbus; Bhupendra C. Trivedi, Worthington, both of Ohio

[73] Assignee: Ashland Oil, Inc., Ashland, Ky.

[21] Appl. No.: 665,467

[22] Filed: Mar. 10, 1976

[51] Int. Cl.$^2$ .......................................... C07D 215/24
[52] U.S. Cl. .............................. 260/289 XA; 423/24
[58] Field of Search ......... 260/289 XA, 619 R, 619 F

[56] References Cited

U.S. PATENT DOCUMENTS 3,637,711  1/1972  Budde et al. ................. 260/289 XA

FOREIGN PATENT DOCUMENTS

75/0412  5/1976  South Africa

OTHER PUBLICATIONS

Beilstein, Handbuch der Organ. Chemie, Band 21, E II System, 3115, p. 71, (1953).
Fuson, "Adv. Org. Chem.", p. 438–442, Wiley, N.Y., (1950).
Tarbell et al., JACS, vol. 64, pp. 607 & 608, (1942).
Hollingshead, "Analyst", vol. 80, pp. 729–735, (1955).

*Primary Examiner*—Donald G. Daus
*Assistant Examiner*—D. B. Springer

[57] ABSTRACT

A class of hydrocarbyl substituted 8-hydroxyquinolines wherein the indicated substituent arises through the direct alkylation of said quinolinol with a ketone obtained by condensing methyl ketone with a hindered aldehyde. These alkylates are useful metal collectors in hydrometallurgical extraction processes designed for the recovery of metal values from dilute aqueous solutions thereof.

10 Claims, No Drawings

7-(ALPHA-METHYL-ALPHA-ALKENYL)SUBSTITUTED 8-HYDROXYQUINOLINES AND PROCESS FOR THE PREPARATION THEREOF

BACKGROUND OF THE INVENTION

1. Field Of The Invention

This invention relates to 8-hydroxyquinoline substituted with an alpha-alkenyl group on the non-hetero ring and to a process for the preparation of such derivatives.

2. Description Of The Prior Art

The compound 8-hydroxyquinoline is well known for its ability to coordinate with ions of a variety of transition metals through covalent bonding to form a relatively stable 5-membered ring which complexes are commonly referred to as metal chelates. This complexing technique has been used extensively heretofore in chemical analytical procedures. Recently, however, the ability of the 8-hydroxy quinoline configuration to form chelates with the transition metals has been utilized in hydrometallurgical extraction processes applicable for the recovery of such metal values from aqueous solutions thereof. These extraction processes comprise basically a two step operation. In the first step an impure aqueous phase containing the desired metal values in ionic form is intimately contacted with a water-immiscible organic solution of the metal collector to facilitate an interfacial relationship of the phases whereby the metal ions are readily and preferentially extracted into the organic phase in the form of a chelate. The second step, which is referred to as stripping, serves to regenerate the extracted metal values in ionic form and to effect the transfer thereof to an aqueous phase thus resulting in a pure and relatively concentrated solution of the desired metal from whence it can then be readily recovered such as by an electrolytic process.

Unfortunately, 8-hydroxyquinoline itself cannot be effectively used in the aforedescribed extraction process because it is not sufficiently soluble in the hydrocarbon solvents employed to provide the organic phase and whereas it is too soluble in the acidic aqueous stripping phases. The deficiencies of 8-hydroxyquinoline in this regard can be overcome, however, by providing a bulky hydrocarbyl substituent thereon which, if properly chosen as to carbon atom content, will markedly enhance its oil-solubility characteristics; and at the same time reduce its solubility even in strong acidic aqueous mediums to essentially a nil value. It is also known that the molecular configuration of such a substituent is quite sensitive from the standpoint of increasing the loading capabilities of the base compound as well as effecting clean and rapid separation of phases particularly in the stripping operation.

A class of 8-hydroxyquinolines modified in the foregoing manner is exemplified in U.S. Pat. No. 3,637,711. These substituted 8-hydroxyquinolines are characterized in having a higher β-alkenyl group in the No. 7 position. The foregoing compounds have proven to be excellent collectors and can be effectively used in all types of metal extraction processes including those requiring a pH range as low as 1-2. Several disadvantages, however, are associated with these prior art extractants. Firstly, their method of preparation calls for the use of a higher allylic chloride which is a difficult and thus a relatively expensive reagent to manufacture. Secondly, their phase separation characteristics when used as a metal extractant desirably stand improvement.

Accordingly, the foremost objective of the present invention is to provide long chain hydrocarbyl 7-substituted derivatives of said quinolinol which represent an improvement over the referred-to prior art extractants in the aspects noted.

SUMMARY OF THE INVENTION

In accordance with this invention a class of alpha alkenyl substituted 8-quinolinols are provided corresponding to the following structural formula:

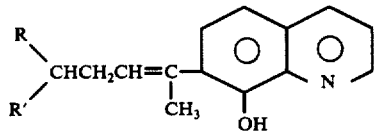

wherein R and R' represent alkyl groups having a sum total of at least four carbon atoms.

In a further aspect, a process is provided for preparing the aforesaid compounds which comprises reacting 8-quinolinol with a ketone having the formula:

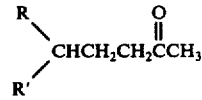

wherein R and R' have the above-mentioned meanings. The foregoing process is carried out at an elevated temperature and under conditions facilitating the removal of water of dehydration ensuing upon, or concominantly generated in effecting the condensation of the ketone and the quinolinol.

DESCRIPTION OF THE PREFERRED EMBODIMENTS

The process contemplated for preparing the novel compounds of the invention calls for the use of a methyl alkyl ketone of the structure noted above for reaction with the 8-quinolinol. These ketones can be readily prepared by reacting equimolar amounts of acetone and a hindered aldehyde in accordance with the standard aldol condensation procedure followed by reducing the resulting condensation product.

The hindered aldehydes useful in the practice of this invention correspond to the following formula:

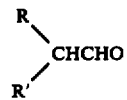

wherein R and R' represent alkyl groups having a sum total of from 4 to 18 carbon atoms. Like the foregoing ketones these aldehydes can be obtained via the aldol condensation procedure but wherein two moles of a starting aldehyde react to form a resultant aldehydic condensate. The applicable starting aldehydes can be either branched or normal. The aldol condensation reaction proceeds to the formation of an alpha-beta unsaturated hindered aldehyde which is then hydrogenated to yield the corresponding saturated species. While this technology and that of the hydroformylation route to a variety of the preferred starting aldehydes from terminal olefins is well understood in the art, the commercial implementation thereof is extremely capital intensive. Accordingly, one is practically constrained to turn to commercial sources of the requisite hindered aldehydes. The foremost source of these aldehydes resides in the commercial production of the "isoalcohols" marketed extensively for use in the plasticizer and cosmetic fields.

Accordingly, one of such aldehydes is 2-ethylhexanol which is a precursor to iso-octanol. It is marketed in a chemically pure form and at a cost in line with availability of the derivative alcohol as a chemical commodity. Likewise, 2,4-diethyloctanol is available commercially and marketed as such in good quality at a reasonable cost. Another similarly available hindered aldehyde is a technical grade of hexadecanol prepared by the aldol condensation of n-octanol in turn obtained by the hydroformylation of heptene1. The foregoing aldehyde is available in the form of the feed stream employed in the OXO process for preparing the alcohol therefrom. Actually, in resorting to a hindered aldehyde such as the aforesaid hexadecanol, it is more expedient to start with the alcohol produced therefrom and reduce same to the aldehyde form by a dehydrogenation step. This is so because the alcohol represents the intended commercial end-product and thus there are certain beneficial purification procedures observed in the manufacture thereof which do not lend themselves to the similar treatment of the precursor aldehyde stream. The dehydrogenation procedure applicable in this instance is very simply carried out aand involves no special equipment requirements.

As previously pointed out, the process contemplated for preparing the compounds of this invention can be characterized as a directed alkylation procedure. In accordance with this procedure the methyl alkyl ketone reacts with the 8-quinolinol to yield what is believed to be a methalol intermediate which will substantially completely dehydrate in situ to provide the resultant alkylate. The reaction scheme for this procedure is outlined as follows where R and R' have the meanings as aforesaid.

260° C. More preferably, the reaction temperature is from 220° to 240° C. The reaction can be carried out in the absence of any reaction diluent in which case means are provided for permitting the water to evolve from the reaction mixture. More preferably, however, the reaction is conducted in the presence of a suitable inert solvent capable of facilitating the azeotropic distillation of the evolved water of dehydration. Toluene and xylol, particularly the latter, represent exemplary solvents for this purpose. Azeotropic distillation is carried out until the evolution of dehydration water essentially completely subsides or a predetermined conversion level has been reached. Thereafter, the alkylate product can advantageously be recovered by simple distillation means. In the distillation recovery of the alkylate product, it is preferred to observe a pressure not in excess of 5 mm Hg while maintaining a pot temperature in the range of from about 150° to 240° C.

While the process aspect of the present invention has been discussed hereinabove strictly in context of the implementation thereof to obtain a particularly effective class of metal extractant, the process is clearly not limited to the production of such compounds. In other words, the process is a relatively general one and adapted to produce a variety of other 7-substituted-8-hydroxyquinolines having usefulness as antioxidants and as chelating agents for preparing fungicide compositions. Accordingly, a variety of other ketones are applicable for carrying out the contemplated alkylation reaction. These include ketones of the formula

wherein R" is H or a hydrocarbyl group, preferably containing from 1 to 21 carbon atoms. Representative of such groups include n-alkyl, alkenyl and aralkyl. The use of several of the foregoing types of ketones will be exemplified in the working examples.

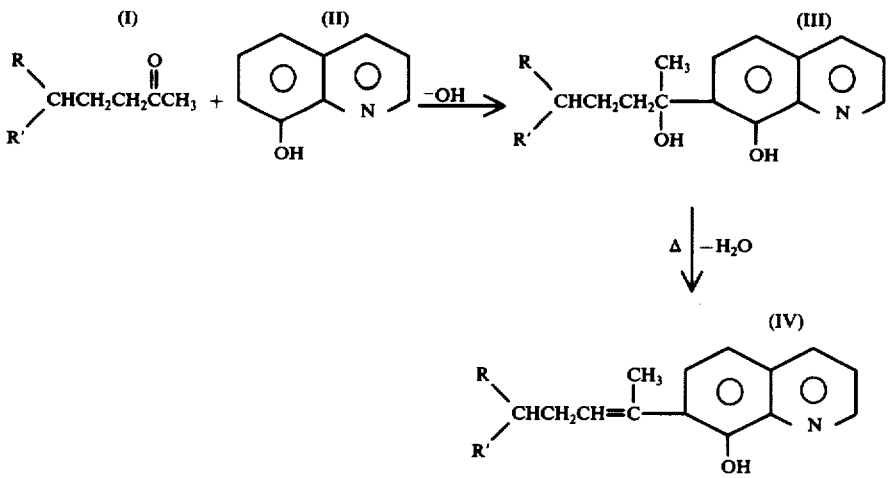

The ketone and the quinolinol are reacted using from 10 to 100% molar excess of the ketone in the presence of a catalytic amount of a strong base such as an alkali metal hydroxide. The preferred combining ratio of the reactants, however, is in the order of 1.5 moles of the ketone per mole of the quinolinol. An applicable temperature range for reacting the ketone and the quinolinol as well as for effecting the dehydration of the resultant methylol intermediate is from about 200° to In order to illustrate to those skilled in the art the best mode contemplated for carrying out the present invention, the following working examples are set forth. As indicated, these examples are given primarily by way of illustration and accordingly, any enumeration of details contained therein should not be interpreted as a limitation on the invention except as such limitations are expressed in the appended claims. All parts and percentages are by weight unless otherwise specified.

EXAMPLE I

Into a suitable reaction vessel equipped with a stirrer, thermometer, reflux condenser and trap for recovering reaction water were charged 849 parts (5.84 moles) of 8-quinolinol and 12.7 parts of potassium hydroxide. With stirring the charge was heated to 200° C. under a nitrogen blanket. While maintaining this temperature, 1494 parts (8.77 moles) of 5-ethyl-2-nonanone were added and the reaction mixture heated to reflux. Water was removed by azeotropic distillation. Reflux was maintained for 11 hours, adding xylene as needed to keep the reaction temperature at or less than 235° C. Following the indicated reaction period, distillation of the mixture was carried out providing a forecut in the amount of 1024 parts, a main cut of alkylate in the amount of 1057 parts and 224 parts of a residue. The forecut consisted of unreacted 8-quinolinol and ketone along with a small amount of xylene. The conversion was 69.1% and the yield realized was 88.1%, both determined by titrating the unreacted 8-quinolinol in the forecut.

EXAMPLE II

Into a reaction vessel equipped as in Example I were charged 49 parts (0.33 mole) of 8-quinolinol, 67 parts (0.337 mole) of 2-tridecanone and 2.5 parts of potassium hydroxide. With stirring the reaction mixture was heated to 250° C. under a nitrogen atmosphere. After 5 hours refluxing at 250° C. with sufficient xylene present at all times to provide a good reflux rate, 3.4 parts of water had collected in the trap whereupon the reaction mixture was cooled. Distillation of the product gave a forecut of 8-quinolinol and unreacted ketone and a main cut of alkylate in the amount of 11 parts.

EXAMPLE III

Into a suitable reaction vessel equipped as in the previous examples were charged 326.9 parts (2.25 moles) of 8-quinolinol and 5.0 parts of potassium hydroxide. The charge was heated under a nitrogen blanket to 140° C. whereupon 366.8 parts (2.45 moles) of 4-phenyl-2-butanone were added and the reaction mixture heated to 250° C. Xylene in the amount of 22 parts was added to provide a good reflux rate. The reaction mixture was held at 250° C. for 12 hours under reflux, then cooled and distilled. A forecut in the amount of 128.3 parts and a main cut in the amount of 230.1 parts were collected. The main cut was redistilled to provide a center cut in the amount of 136.3 parts exhibiting a b.p. 145°–155° C. at 0.4mm.

EXAMPLE IV

The purpose of this example is to illustrate the effectiveness of a representative compound of this invention as a metal extractant. The illustration will be confined to the static extraction, stripping and phase separation of copper solutions in the presence of a surface active modifier, the use of which is conventionally observed in dynamic operations.

EXTRACTION

An organic phase (ESCAID 200) containing 5 vol. % of the alkylate of Example I and 12.5 vol. % of nonylphenol as the modifier was contacted for 2 minutes at room temperature in a separatory funnel with an aqueous solution containing 4.1 grams per liter (gpl) copper and having a pH of 1.5. Two volumetric organic to aqueous (O/A) phase ratios were observed. The loading capacity of the organic phase in this instance was 3.9 gpl Cu. The results are tabulated as follows:

| O/A | Aqueous Cu conc. (gpl) | Organic Cu conc. (gpl) | % Cu Extracted |
|---|---|---|---|
| 2 | .77 | 1.72 | 81.2 |
| 1 | 1.28 | 2.82 | 68.8 |

An organic phase as above containing 5 vol. % of the alkylate of Example I and 12.5 vol. % of nonylphenol was similarly contacted for 1 minute. with an aqueous solution containing 4.10 gpl Cu and having a pH of 1.5. The organic loading capacity was 3.9 gpl Cu. The results are tabulated as follows:

| O/A | Aqueous Cu conc (gpl) | Organic Cu conc (gpl) | % Cu Extracted |
|---|---|---|---|
| 2 | .83 | 1.64 | 79.6 |
| 1 | 1.35 | 2.75 | 67.1 |

STRIPPING

An organic phase containing 5 vol. % of the alkylate of Example I and 12.5 vol. % nonylphenol was loaded to contain 3.37 gpl Cu. The loaded organic phase was then contacted with a like volume of an aqueous stripping solution containing 25 gpl Cu and 155 gpl conc. $H_2SO_4$. After contact for 2 minutes the phases were allowed to separate. The copper content of the organic phase was found to be 0.15 gpl indicating that over 96% of the copper was stripped.

An organic phase containing 5 vol. % of the alkylate of Example I and otherwise similar to that above was loaded to contain aproximately 3 gpl Cu. The loaded organic phase was contacted with a like volumetric amount of an aqueous stripping solution containing 123 gpl conc. $H_2SO_4$ and 24.8 gpl Cu. After stripping contact for 2 minutes, the copper content of the organic phase was reduced to 0.30 gpl.

PHASE-SEPARATION

Extraction phase separation was conducted by contacting 500 ml of a 5 vol. % of the alkylate of Example I and a 12.5 vol. % nonylphenol in ESCAID 200 with 500 ml of a 3 gpl copper aqueous solution having a pH of 1.2 in a 1 liter graduated cylinder. The two phases were dispersed at room temperature for 2 minutes with the aid of a mechanical stirrer. Complete phase separation occurred in 5'45" after mixing was terminated.

For stripping phase separation, the above organic phase was contacted for 1 minute with an aqueous stripping solution consisting of 140 gpl conc. $H_2SO_4$ and 24.8 gpl Cu in the same manner as above. Complete separation occurred in 5 minutes.

Extraction phase separation of the alkylate of Example I was run under the same conditions as above. Phase separation time was 4'45". Stripping phase separation was also run in the same manner with the exception that the stripping solution contained 218 gpl conc $H_2SO_4$ and 25 gpl Cu. Phase separation time was 17'45".

What is claimed is:

1. A compound of the formula

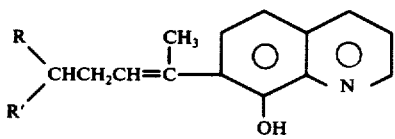

wherein R and R' represent alkyl groups having a sum total of from 4–18 carbon atoms.

2. The compound in accordance with claim 1 wherein R is butyl and R' is ethyl.

3. The compound in accordance with claim 1 wherein R is 2-ethylhexyl and R' is ethyl.

4. A compound in accordance with claim 1 wherein R is a $C_6H_{13}$ alkyl group and R' is a $C_8H_{17}$ alkyl group.

5. A process for preparing 7-(alpha-methyl-alpha-alkenylates) of 8-hydroxyquinoline which comprises reacting at a temperature of from about 200°–260° C. one mole of 8-hydroxyquinoline with from 1.1 to 2 moles of a ketone of the formula:

wherein R" represents H or a $C_1$ – $C_{21}$ hydrocarbyl group, to effect the condensation of said reactants and the concomitant removal of water of dehydration from the condensate and thereupon distilling the reaction product to recover the resultant alkenylate.

6. A process in accordance with claim 5 wherein said ketone corresponds to the formula:

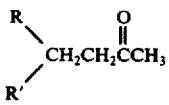

where R and R' represent alkyl groups having a sum total of from 6–18 carbon atoms.

7. A process in accordance with claim 6 wherein the reaction temperature is from 220°–240° C.

8. A process in accordance with claim 7 wherein R of said ketone is butyl and R' is ethyl.

9. A process in accordance with claim 8 wherein the molar ratio of 8-hydroxyquinoline to said ketone is 1:1.5, respectively.

10. A process in accordance with claim 9 wherein the removal of water is effected by azeotropic distillation.

* * * * *